US00PP14014P29

(12) United States Plant Patent
Heims

(10) Patent No.: US PP14,014 P2
(45) Date of Patent: Jul. 22, 2003

(54) PULMONARIA PLANT NAMED 'MOUNTAIN MAGIC'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/170,825

(22) Filed: Jun. 12, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Pulmonaria plant characterized by vigor, silver blotched and spotted leaves and large, open, purple to violet flowers.

2 Drawing Sheets

Botanical classification: Pulmonaria hybrid.
Variety denomination: 'Mountain Magic'.

BACKGROUND OF THE INVENTION

The present invention relates to a new and distinct cultivar of a hardy perennial of the genus Pulmonaria, and known by the cultivar name 'Mountain Magic'. The genus Pulmonaria is a member of the family Boraginaceae.

The new cultivar originated as an open-pollinated cross between unknown parents in a field of selected hybrid Pulmonaria. This is known to be an outcross because Pulmonaria does not normally self-pollinate. Due to the fact that the instant plant and parent plants are interspecific hybrids from several generations of interbreeding and selecting, no species designations are given.

SUMMARY OF THE INVENTION

This new cultivar is characterized by:

1) Strong purple to brilliant violet colored flowers;
2) Upfacing flowers;
3) Large flower size;
4) Foliage with prominent silver spotting and blotching.
5) Undulating leaf margins;
6) Medium, compact habit;
7) Excellent vigor.

This new cultivar has been reproduced only by asexual propagation (division and tissue culture). The tissue culture method used is micropropagation from the axillary buds. Each of the progeny exhibits identical characteristics to the original plant. Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
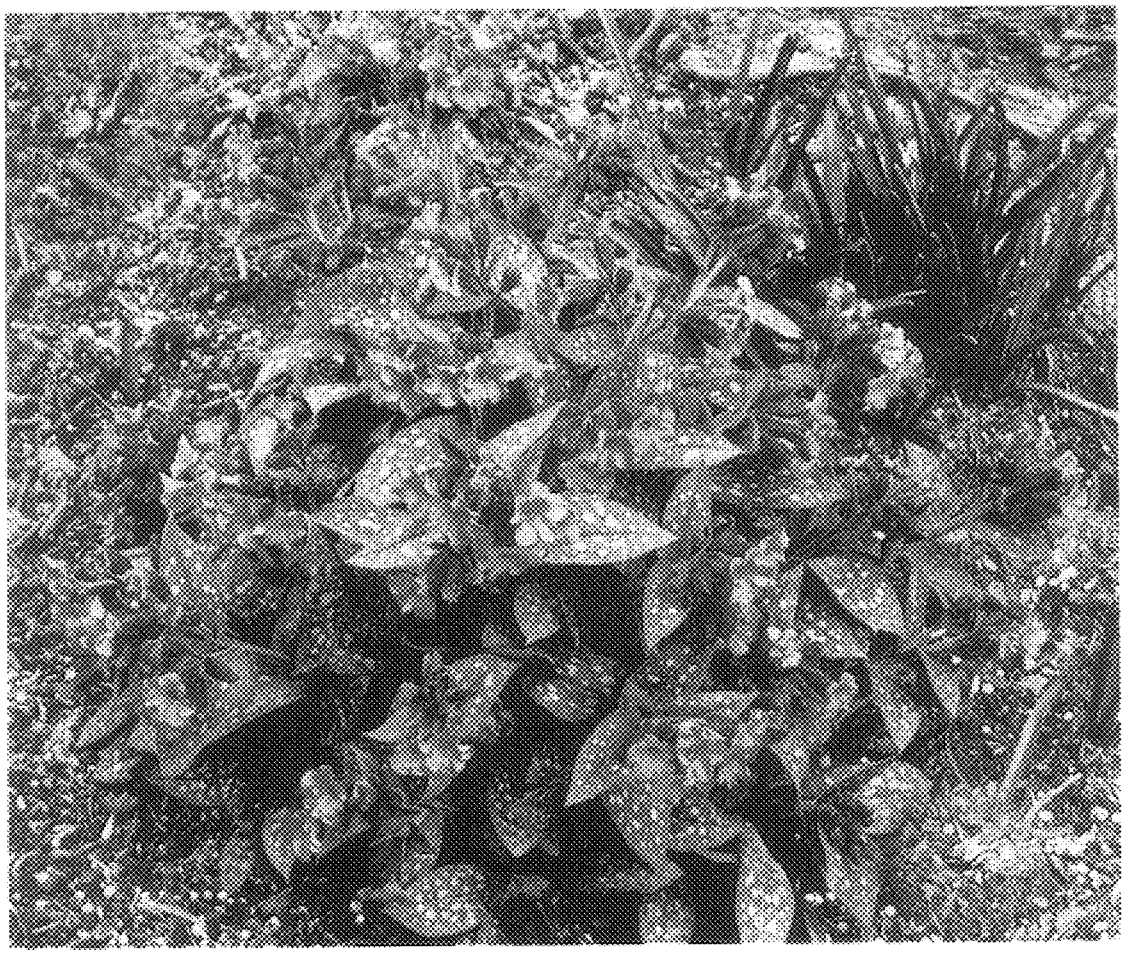
FIG. 1 shows Pulmonaria 'Mountain Magic' in flower in the spring growing in the ground in Canby, Oreg.
Figure 2:
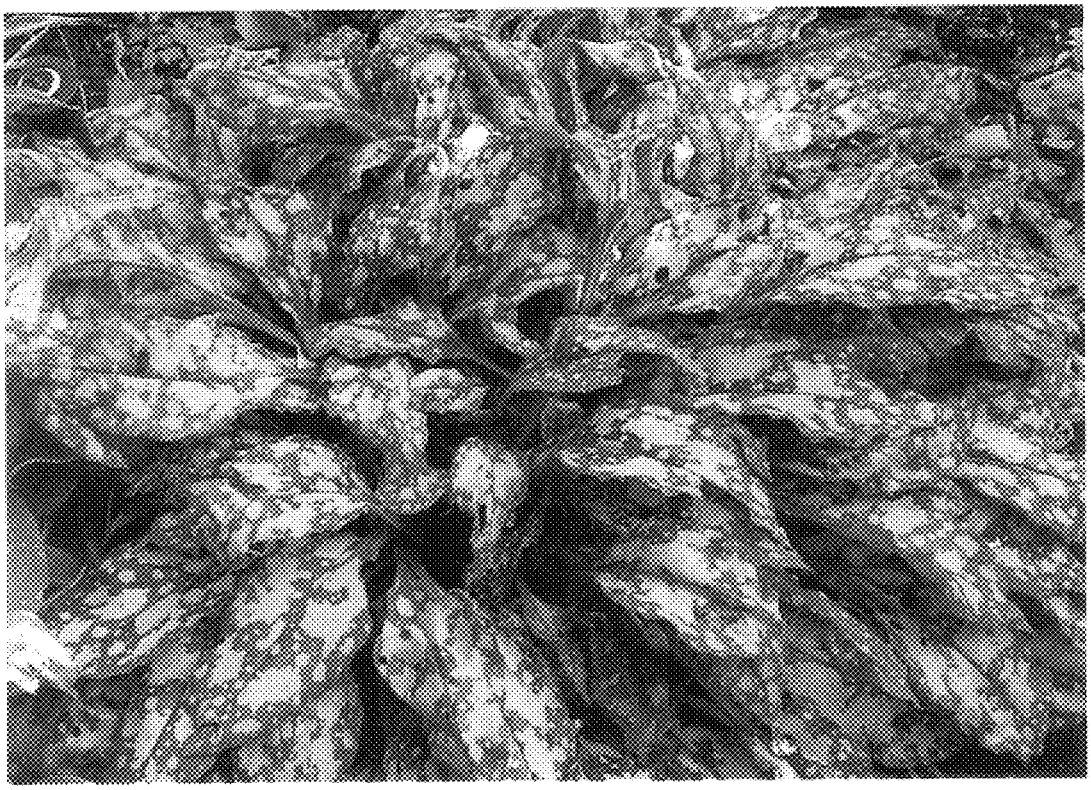
FIG. 2 shows the summer foliage.

The following is a detailed description of the new Pulmonaria hybrid based on observations of two-year-old specimens grown in the ground in Canby, Oreg. The color descriptions are all based on The Royal Horticultural Society Colour Chart.

Botanical name: Pulmonaria hybrid.
Cultivar name: 'Mountain Magic'.
Plant:
- *Type.*—Herbaceous perennial.
- *Hardiness.*—USDA Zones 5 to 9.
- *Spring size.*—45 cm. wide and 25 cm. tall.
- *Summer size.*—50 cm. wide and 26 cm. tall.
- *Form.*—Rounded basal clump.

Leaf:
- *Type.*—Simple.
- *Shape.*—Elliptic to oblanceolate.
- *Arrangement.*—Rosette.
- *Blade length.*—18 to 20 cm.
- *Blade width.*—7 to 7.5 cm. at widest point.
- *Margins.*—Undulate and occasionally irregularly serrate.
- *Apex.*—Acuminate.
- *Base.*—Attenuate.
- *Venation.*—Pinnate.
- *Vestiture.*—Scabrous and sparingly glandular.
- *Texture.*—Rough and leathery.
- *Petiole length.*—14 to 16 cm.
- *Petiole texture.*—Scabrous.
- *Petiole color.*—Yellow Green 148C.
- *Color.*—Topside: Deep green, between Green 137A and 138A, blotched and spotted silver, Greyed Green 194A. Bottom: Closest to Yellow Green 147B.

Cauline leaves (These are found in the spring only on the flowering stems. After the seed is produced these stems die out.):
- *Type.*—Simple.
- *Arrangement.*—Alternate.
- *Shape.*—Variable. Elliptic, obovate, or ovate.
- *Length.*—5 to 9 cm.
- *Width.*—2.5 cm.
- *Margins.*—Undulate.
- *Apex.*—Acuminate.
- *Base.*—Clasping, sessile.

*Leaf texture.*—Hispid.
*Venation.*—Pinnate.
*Color.*—Topside: Deep green, Green 137C with silver spots, Greyed Green 193A. Bottom side: Closest to 147B.

Inflorescence:
*Type.*—Terminal forked cyme.
*Number of flowers per cyme.*—13.
*Peduncle.*—Height: 20 to 27 cm. Diameter: 3.5 mm. Texture: Hispid.
*Color.*—Yellow Green 146D.
*Pedicel.*—Length: Varies. 0.5 to 2 cm. Texture: Hispid.
*Color.*—Yellow Green 146B at base changing to Brown 200C close to the flowers.

Flower bud:
*Size.*—1.6 cm. long and 0.4 cm. wide.
*Shape.*—Ovoid.
*Color.*—Red maroon, Greyed Purple 185B.

Flower:
*Type.*—Actinomorphic.
*Shape.*—Funnelform.
*Size.*—2.3 cm. deep and 1.7 cm wide.
*Corolla.*—5 fused petals with rounded lobes.
*Color.*—Changes with age from red maroon, Greyed Purple 185B, to purple, Purple Violet 82B to violet, Violet Blue 92A.
*Calyx.*—5 fused sepals, tubular campanulate, parted ⅓ to base, hispid.
*Calyx size.*—1.6 cm deep and 0.6 cm wide.
*Calyx color.*—Closest to Brown 200B.
*Pistil.*—1.3 cm., pin type, exerted from corolla tube.
*Ovary position.*—Partly inferior.
*Carpel number.*—4.
*Stamen number.*—5, attached to and inserted in the tube.
*Pollen color.*—White 155C.
*Bloom period.*—April to May in Canby, Oreg.
*Fragrance.*—None.

Seed:
*Type.*—4 smooth nutlets, Black 202A and shiny, typical of the genus.
*Fertility.*—Low.

Disease: None observed on plant grown under commercial conditions in Canby, Oreg.

COMPARISONS TO SIMILAR PULMONARIA

Compared to Pulmonaria 'May Bouquet', (U.S. Plant Pat. No. 12,336), Pulmonaria 'Mountain Magic' has violet colored flowers rather than blue, and longer leaves and petioles. Their habits and leaf colorations are similar.

Compared to Pulmonaria 'Dark Vader' (U.S. Plant Pat. No. 12,333), this new cultivar has larger, more open flowers maturing to a violet color rather than a deep blue, more silvering on the leaves, and is of a pin type pistil rather than a thrum.

Compared to Pulmonaria 'High Contrast' (U.S. Plant Pat. No. 12,337), this new cultivar has purple to violet colored flowers rather than pink to blue colored flowers and a more compact habit.

I claim:

1. A new and distinct hybrid of Pulmonaria plant substantially as shown and described.

* * * * *